(12) United States Patent
Tan

(10) Patent No.: US 8,784,358 B2
(45) Date of Patent: Jul. 22, 2014

(54) INTELLIGENT AUTOMATIC PERITONEAL DIALYSIS

(76) Inventor: Ta-Lun Tan, Taipei (TW)

( * ) Notice: Subject to any disclaimer, the term of this patent is extended or adjusted under 35 U.S.C. 154(b) by 534 days.

(21) Appl. No.: 13/015,476

(22) Filed: Jan. 27, 2011

(65) Prior Publication Data

US 2011/0184339 A1    Jul. 28, 2011

(30) Foreign Application Priority Data

Jan. 27, 2010 (TW) ................................ 99102278 A

(51) Int. Cl.
*A61M 1/00* (2006.01)
(52) U.S. Cl.
USPC ................................ 604/29; 604/28; 604/31
(58) Field of Classification Search
USPC .......................................... 604/27–35, 43–45
See application file for complete search history.

(56) References Cited

U.S. PATENT DOCUMENTS

| 3,709,222 | A  | * | 1/1973 | DeVries ........................... 604/28 |
| 5,213,571 | A  | * | 5/1993 | Fujio et al. ...................... 604/31 |
| 5,556,378 | A  | * | 9/1996 | Storz et al. ...................... 604/31 |
| 7,544,300 | B2 | * | 6/2009 | Brugger et al. ............... 210/645 |
| 2008/0006096 | A1 | * | 1/2008 | Gordon et al. ............. 73/861.43 |

* cited by examiner

*Primary Examiner* — Kami A Bosworth
(74) *Attorney, Agent, or Firm* — Osha Liang LLP

(57) ABSTRACT

An intelligent automatic peritoneal dialysis device injects a dialysate accommodated in a dialysate container into a live animal via an input duct, elicits a waste liquid from the animal via an output duct, and concentrates the waste liquid in a waste liquid container. A flow direction control valve controls the flow direction of the dialysate and the waste liquid during the overall peritoneal dialysis treatment process.

10 Claims, 9 Drawing Sheets

INTELLIGENT AUTOMATIC PERITONEAL DIALYSIS

BACKGROUND OF THE INVENTION

1. Field of the Invention

The present invention relates to an intelligent automatic peritoneal dialysis device, and more particularly to a peritoneal dialysis device performing peritoneal dialysis on animals.

2. Description of Related Art

Conventional peritoneal dialysis devices are designed for humans. The same peritoneal dialysis duct delivers dialysate into a human body and drains waste liquid from the human body. Hence, the dialysate and the waste liquid alternatively pass through the same peritoneal dialysis duct. Moreover, the peritoneal dialysis duct has a fixed length and can hold 0.1 liter of liquid volume.

A peritoneal cavity of an adult may readily accommodate two liters of dialysate. When two liters of dialysate are delivered through the peritoneal dialysis duct after two liters of waste liquid are drained via the peritoneal dialysis duct, the initial 0.1 liter of dialysate flowing through the peritoneal dialysis duct is used to clean the peritoneal dialysis duct. The remainder of the 1.9 liters of dialysate lowers the efficiency of peritoneal dialysis after having been injected into the human body. Therefore, the dialysis efficiency of conventional peritoneal dialysis devices for the human body is 95%.

Since a peritoneal cavity of an animal merely accommodates 0.5 liter of dialysate, when 0.5 liter of dialysate flows through the peritoneal dialysis duct after 0.5 liter of waste liquid flows through the peritoneal dialysis duct, the initial 0.1 liter of dialysate flowing through the peritoneal dialysis duct is used to clean the peritoneal dialysis duct and the remaining 0.4 liter of dialysate lowers the efficiency of peritoneal dialysis after having been injected into the animal. Therefore, when a conventional peritoneal dialysis device designed for the human body is applied to an animal, the dialysis efficiency is 80%. As the peritoneal cavity may accommodate less dialysate if the animal is smaller, dialysis efficiency may be further lowered.

Additionally, more and more waste liquid will accumulate in the body and cause patient discomfort when the peritoneal dialysis duct of a conventional peritoneal dialysis device is restricted such that the waste liquid cannot be smoothly drained from the body while the dialysate keeps flowing into the body. Under this condition, if the conventional peritoneal dialysis device is applied to the human, the patient himself may forcibly interrupt the operation of the peritoneal dialysis device by manual regulation to stop the dialysate from being delivered into the body. However, when a conventional peritoneal dialysis device is applied to an animal and obstruction is encountered, the animal itself cannot interfere in the operation of the peritoneal dialysis device by manual regulation to stop the dialysate from being delivered into the body. Hence, more and more waste liquid will accumulate in an animal resulting in death.

A need therefore exists for dialysis devices with improved efficiency and the capability of automatically troubleshooting. A particular need exists for such improved dialysis devices which can perform intelligently and automatically, and solve the problems mentioned above.

SUMMARY

An aspect of the present disclosure is an intelligent automatic peritoneal dialysis device having a first duct and a second duct such that a dialysate and a waste liquid flow through different ducts, respectively, thereby improving dialysis efficiency.

Another aspect of the present disclosure is an intelligent automatic peritoneal dialysis device having a flow direction control valve and a plurality of monitoring devices such that the dialysis device may automatically control the flow direction of the dialysate and the waste liquid when a fault occurs, without external intervention. Hence, embodiments of the present disclosure may effectively solve the previously described problems.

Additional aspects and other features of the present disclosure will be set forth in the description which follows and in part will be apparent to those having ordinary skill in the art upon examination of the following or may be learned from the practice of the present disclosure. The advantages of the present disclosure may be realized and obtained as particularly pointed out in the appended claims.

Embodiments of the present disclosure provide an intelligent automatic peritoneal dialysis device structured to inject a dialysate accommodated in a dialysate container into a live animal, elicit a waste liquid from the animal, and concentrate the waste liquid in a waste liquid container. Embodiments include an intelligent automatic peritoneal dialysis comprising: a flow direction control valve used to control the flow direction of the dialysate and the waste liquid, the flow direction control valve having a first valve, a second valve and a third valve; an input duct connected to the dialysate container and the first valve, the input duct causing the dialysate to flow from the dialysate container into the flow direction control valve; an output duct connected to the waste liquid container and the second valve, the output duct causing the waste liquid to flow from the flow direction control valve into the waste liquid container; a communication duct connected to the input duct and the output duct, wherein the third valve is disposed in the communication duct; a first duct connected to the first valve and the animal; and a second duct connected to the second valve and the animal.

Embodiments of the present disclosure also provide methods of operating a previously described intelligent automatic peritoneal dialysis device. Embodiments of the present disclosure include a method comprising: (a) opening the first valve and the second valve while closing the third valve; (b) causing the dialysate from the dialysate container to flow through the input duct, the first valve and the first duct, and be injected into the animal; and (c) causing the waste liquid from the animal to flow through the second duct, the second valve and the output duct, and be injected into the waste liquid container.

Embodiments of the present disclosure further include a method comprising: (a) closing the first valve while opening the second valve and the third valve; (b) causing the dialysate from the dialysate container to flow through the input duct, the communication duct, the third valve, the second valve and the second duct, and be injected into the animal; (c) opening the first valve and the third valve while closing the second valve; and (d) causing the waste liquid from the animal to flow through the first duct, the first valve, the communication duct, the third valve and the output duct and be injected into the waste liquid container.

Embodiments of the present disclosure further provide a method comprising: (a) opening the first valve while closing the second valve and the third valve; (b) causing the dialysate from the dialysate container to flow through the input duct, the first valve and the first duct, and be injected into the animal; (c) opening the first valve, the second valve and the third valve; and (d) causing the waste liquid from the animal to flow through the first duct, the first valve, the communication duct, the third valve and the output duct, and be injected into the waste liquid container while at the same time, the waste liquid from the animal may also flow through the second duct, the second valve and the output duct and be injected into the waste liquid container.

Embodiments of the present disclosure additionally provide a method comprising: (a) closing the first valve while opening the second valve and the third valve; (b) causing the dialysate from the dialysate container to flow through the input duct, the third valve, the second valve and the second duct, and be injected into the animal; (c) opening the first valve, the second valve and the third valve; and (d) causing the waste liquid from the animal to flow through the first duct, the first valve, the communication duct, the third valve and the output duct, and be injected into the waste liquid container while at the same time, the waste liquid from the animal also flow through the second duct, the second valve and the output duct and be injected into the waste liquid container.

Intelligent automatic peritoneal dialysis devices in accordance with embodiments of the present disclosure include first and second ducts such that the dialysate and the waste liquid pass through different ducts, respectively, thereby improving dialysis efficiency. Additionally, intelligent automatic peritoneal dialysis devices in accordance with embodiments of the present disclosure include a flow direction control valve and a plurality of monitoring devices such the flow direction of the dialysate and the waste liquid are automatically controlled should a fault occur.

Additional aspects and technical effects of the present disclosure will become readily apparent to those skilled in the art from the following detailed description wherein embodiments of the present disclosure are described simply by way of illustration of the best mode contemplated to carry out the present disclosure. As will be realized, the present disclosure is capable of other and different embodiments, and its several details are capable of modifications in various obvious respects, all without departing from the present disclosure. Accordingly, the drawings and description are to be regarded as illustrative in nature, and not as restrictive.

BRIEF DESCRIPTION OF DRAWINGS

The present disclosure is illustrated by way of example, and not by way of limitation, in the figures of the accompanying drawing and in which like reference numerals refer to similar elements and in which.

DETAILED DESCRIPTION

In the following description, for the purposes of explanation, numerous specific details are set forth in order to provide a thorough understanding of exemplary embodiments. It should be apparent, however, that exemplary embodiments may be practiced without these specific details or with an equivalent arrangement. In other instances, well-known structures and devices are shown in block diagram form in order to avoid unnecessarily obscuring exemplary embodiments. In addition, unless otherwise indicated, all numbers expressing quantities, ratios, and numerical properties of ingredients, reaction conditions, and so forth used in the specification and claims are to be understood as being modified in all instances by the term "about."

Embodiments of the present disclosure provide intelligent automatic peritoneal dialysis devices which are widely applicable to the dialysis treatment of all kinds of animals. In addition, related combinations of implementation methods are numerous. Therefore, specific disclosed embodiment are merely exemplarily and not intended as all inclusive of other combinations.

Figure 1:
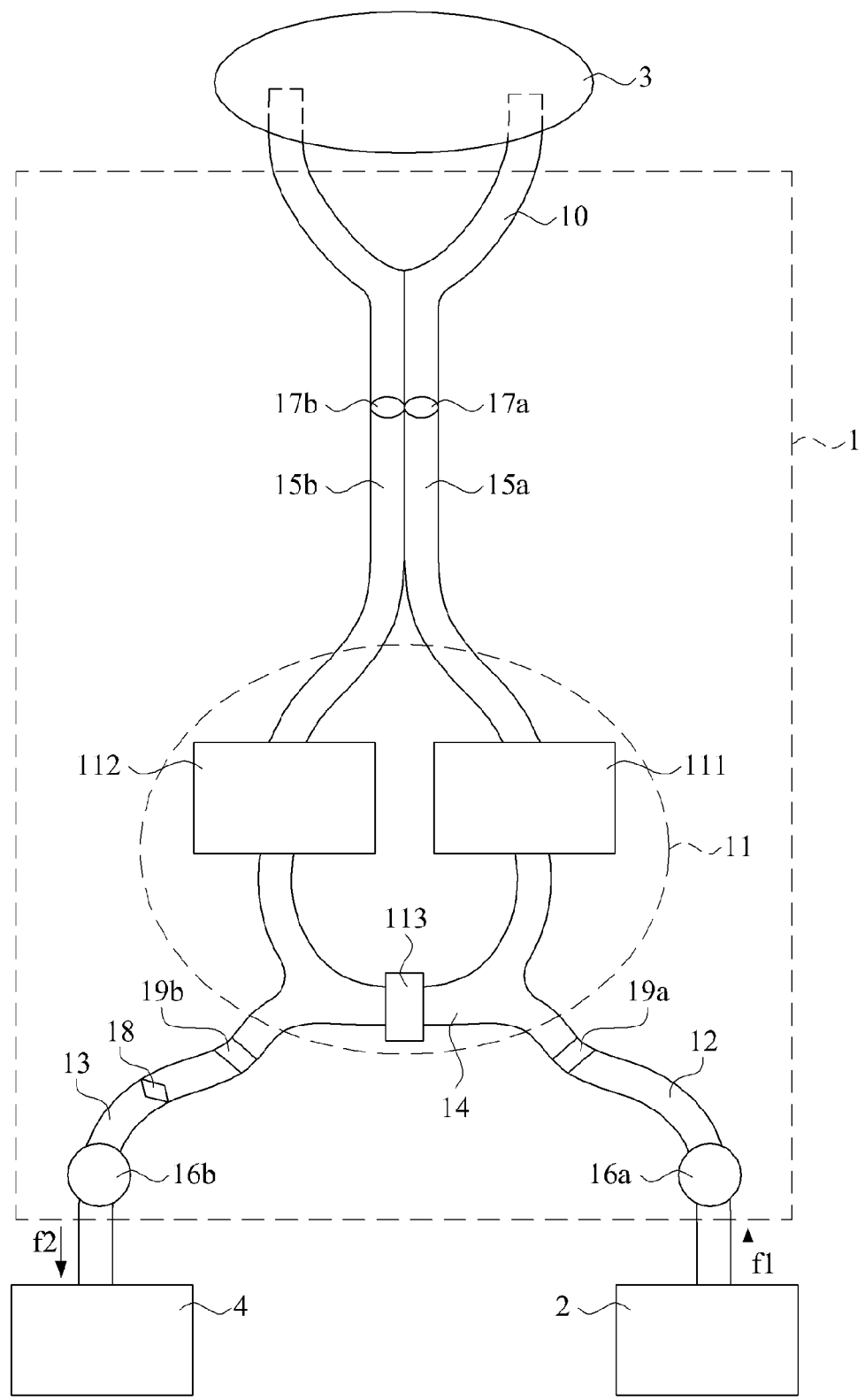
FIG. 1 schematically illustrates a dialysis device in accordance with an embodiment of the present disclosure.

The intelligent automatic peritoneal dialysis device 1 schematically illustrated in FIG. 1 may be employed to inject a dialysate f1, accommodated in a dialysate container 2, into a live animal 3, elicit a waste liquid f2 from the animal 3, and concentrate the waste liquid f2 in a waste liquid container 4. The intelligent automatic peritoneal dialysis device 1 comprises a flow direction control valve 11, an input duct 12, an output duct 13, a communication duct 14, a first duct 15a, a second duct 15b, a first motor 16a, a second motor 16b, a first pressure sensor 17a, a second pressure sensor 17b, a flow sensor 18, a first air sensor 19a, a second air sensor 19b and a Y-type duct joint 10.

The flow direction control valve 11 may comprise a first valve 111, a second valve 112 and a third valve 113. The third valve 113 may be disposed in the communication duct 14. The flow direction control valve 11 is used to control the flow direction of the dialysate f1 and waste liquid f2. The first valve 111, the second valve 112 and the third valve 113 may be turned-on and turned-off automatically or manually. The flow direction control valve 11 may be a magnetic control switch, a digital control switch or a mechanical control switch.

The input duct 12 may be connected to the dialysate container 2 and the first valve 111. The input duct 12 may be used to cause the dialysate f1 to flow from the dialysate container 2 to the flow direction control valve 11.

The output duct 13 may be connected to the waste liquid container 4 and the second valve 112. The output duct 13 may be used to cause the waste liquid f2 to flow from the flow direction control valve 11 to the waste liquid container 4.

The communication duct 14 may be connected to the input duct 12 and the output duct 13. The first duct 15a may be connected to the first valve 111 and the animal 3. The second duct 15b may be connected to the second valve 112 and the animal 3.

The first motor 16a may be disposed between the dialysate container 2 and the input duct 12. The dialysate f1 may flow from the dialysate container 2 to the input duct 12 by operation of the first motor 16a.

The second motor 16b may be disposed between the waste liquid container 4 and the output duct 13. The waste liquid f2 may flow from the output duct 13 to the waste liquid container 4 by operation of the second motor 16b.

The first pressure sensor 17a may be disposed in the first duct 15a. The first pressure sensor 17a may be used to monitor the pressure of the animal 3 so as to regulate the operation speed of the first motor 16a or the operation speed of the second motor 16b.

The second pressure sensor 17b may be disposed in the second duct 15b. The second pressure sensor 17b may be used to monitor the pressure of the animal 3 so as to regulate the operation speed of the first motor 16a or the operation speed of the second motor 16b.

The flow sensor 18 may be disposed in the output duct 13. The flow sensor 18 may be used to monitor the flow of the waste liquid f2 flowing through the output duct 13 so as to regulate the operation speed of the second motor 16b.

The first air sensor 19a may be disposed in the input duct 12. The first air sensor 19a may be used to monitor whether the dialysate f1 flowing through the input duct 12 contains air or not.

The second air sensor 19b may be disposed in the output duct 13. The second air sensor 19b may be used to monitor whether the waste liquid f2 flowing through the output duct 13 contains air or not.

The Y-type duct joint 10 has one end connected to the first duct 15a and the second duct 15b and the other end extending into the animal 3.

The previously described flow direction control valve 11, first motor 16a, second motor 16b, first pressure sensor 17a, second pressure sensor 17b, flow sensor 18, first air sensor 19a and second air sensor 19b may further be connected to an electronic device (not shown) and a display device (not shown) such that the previously described sensors may deliver a monitoring signal (not shown) to the electronic device and the display device according to the monitored operating conditions so as to cause the electronic device to regulate the flow direction control valve 11, the first motor 16a and the second motor 16b according to the monitoring signal. The electronic device may be a computer.

Moreover, the display device may display the operating condition of the intelligent automatic peritoneal dialysis device 1 according to the monitoring signal. The display device may be a liquid crystal screen.

Several operative methods in accordance with embodiments of the present disclosure are exemplarily illustrated below.

Example 1

The first valve 111 and the second valve 112 are initially opened and the third valve 113 is closed when the operation method is performed. Next, the first motor 16a is started such that the dialysate f1 flows from the dialysate container 2 to the input duct 12, the first air sensor 19a, the first valve 111, the first duct 15a, the first pressure sensor 17a and the Y-type duct joint 10. The dialysate f1 is then injected into the live animal 3.

The dialysate f1 may remain in the animal 3 for a period of time. A diffusion exchange and an osmosis exchange take place in the animal 3 via a peritoneum of the animal 3 while the dialysate f1 remains in the animal 3. Therefore, waste products in the blood will pass through blood capillaries on the peritoneum and enter the dialysate f1. The waste liquid f2 will be formed after a period of time.

Next, the waste liquid f2 may flow from the animal 3 to the Y-type duct joint 10, the second duct 15b, the second pressure sensor 17b, the second valve 112, the output duct 13, the second air sensor 19b and the flow sensor 18, and finally be injected into the waste liquid container 4 by gravity or by starting the second motor 16b.

The method of this example is a continuous peritoneal dialysis method, wherein the dialysate f1 is injected into the animal 3 and the waste liquid f2 is automatically elicited from the animal 3 after the dialysate f1 remains in the animal 3 for a period of time.

Additionally, this method is also applicable to a continuous peritoneal dialysis, wherein the dialysate f1 is injected into the animal 3 and the waste liquid f2 is elicited from the animal 3, simultaneously, by starting the first motor 16a and the second motor 16b at the same time and regulating the operation speed of the first motor 16a and the second motor 16b, respectively.

The operation speed of the first motor 16a may be adjusted to be slower, the first motor 16a may stop or the operation speed of the second motor 16b may be adjusted to run faster than the first motor 16a when the first pressure sensor 17a and the second pressure sensor 17b monitor a high pressure that the pressure of the animal 3 such that the dialysate f1 is injected into the animal 3 with a lower flow speed, the dialysate f1 stops been injected into the animal 3 or the waste liquid f2 is elicited from the animal 3 with a higher flow speed. For example, an excessively high pressure will be generated in the animal 3 such that the animal feels uncomfortable and even faces a life-threatening situation when the dialysate f1 injected into the animal 3 is too much and the waste liquid f2 remaining in the animal 3 is also too much. Therefore, the previously described problems may be avoided by monitoring the first pressure sensor 17a and the second pressure sensor 17b.

In addition, the operation speed of the second motor 16b will be regulated to be faster when the flow sensor 18 monitors too little flow or too low flow speed of the waste liquid f2 passing through the output duct 13, so as to raise the flow or the flow speed of the waste liquid f2. For example, non-liquid substances (for instance, adipose tissue) found in the waste liquid f2 may cause blockage of the duct resulting in reduced flow volume or low flow speed. Another example is failure of draining waste liquid f2 from the animal 3 using gravity, resulting in insufficient flow volume via the output duct 13 or low flow speed. Therefore, the previously described problems can be avoided by monitoring the function of the flow sensor 18.

Moreover, the first valve and the second valve are closed and the third valve is opened when the first air sensor 19a monitors the dialysate f1 of the input duct 12 containing air so as to cause the air to sequentially pass through the communication duct 14, the third valve 113, the output duct 13, the second air sensor 19b and the flow sensor 18. Finally, the air will be exhausted to a region outside of the intelligent automatic peritoneal dialysis device 1. As the animal will feel uncomfortable when the dialysate f1 injected into the animal 3 contains air, the previously described problems may be avoided by monitoring of the first air sensor 19a.

The first valve 111, the second valve 112 and the third valve are closed and an alarm signal is delivered when the second air sensor 19b monitors the pressure of air in the waste liquid f2 of the output duct 13 containing air so as to notify medical staff. For example, air may enter the animal 3 via a broken hole on the duct or an incorrect connection of the ducts when the animal bites the duct or the ducts are incorrectly connected. In such event, the animal will have a peritonitis crisis of potentially fatal consequence. Therefore, the previously described problems may be avoided by monitoring of the second air sensor 19b.

In this method, if the problems of too little flow or too low flow speed of the waste liquid f2 are still not improved after the operation speed of the second motor 16b is regulated, the previously described problems may be solved by a second application example of an embodiment of the present disclosure.

Example 2

Initially, the first valve 111 is closed and the second valve 112 and the third valve 113 are opened when the method is performed. Next, the first motor 16a is started such that the dialysate f1 flows from the dialysate container 2 to the input duct 12, the first air sensor 19a, the communication duct 14, the third valve 113, the second valve 112, the second duct 15b, the second pressure sensor 17b and the Y-type duct joint 10. Finally, the dialysate f1 is injected into the live animal 3.

The dialysate f1 may remain in the animal 3 for a period of time. The diffusion exchange and the osmosis exchange may be performed in the animal 3 via the peritoneum of the animal 3 during the dialysate f1 remaining in the animal 3. Therefore, the waste products in the blood will pass through the blood capillaries on the peritoneum and enters the dialysate f1. The waste liquid f2 will be formed after a period of time.

Next, the first valve 111 and the third valve 113 are opened and the second valve 112 is closed. Then the waste liquid f2 may flow from the animal 3 to the Y-type duct joint 10, the first duct 15a, the first pressure sensor 17a, the first valve 111, the communication duct 14, the third valve 113, the output duct 13, the second air sensor 19b and the flow sensor 18 and finally be injected into the waste liquid container 4 by using the gravity head or starting the second motor 16b.

The operating modes of the first pressure sensor 17a, the second pressure sensor 17b, the flow sensor 18, the first air sensor 19a and the second air sensor 19b are similar to those of the EXAMPLE 1, above and, therefore, not here repeated.

The method of this example is a continuous cycle peritoneal dialysis. If the problem of too much dialysate f1 and waste liquid f2 in the animal 3 is still not improved after lowering the operation speed of the first motor 16a and increasing the operation speed of the second motor 16b when excessive amount of the dialysate f1 injected in the animal 3 and excessive amount of retained the waste liquid f2 remaining in the animal 3, the previously described problem may be solved by a third application example of an embodiment of the present disclosure.

Example 3

Initially, the first valve 111 is opened and the second valve 112 and the third valve 113 are closed when the method is performed. Next, the first motor 16a is started such that the dialysate f1 flows from the dialysate container 2 to the input duct 12, the first air sensor 19a, the first valve 111, the first duct 15a, the first pressure sensor 17a and the Y-type duct joint 10. Finally, the dialysate f1 is injected into the live animal 3.

The dialysate f1 may remain in the animal 3 for a period of time. The diffusion exchange and the osmosis exchange take place in the animal 3 via the peritoneum of the animal 3 while the dialysate f1 remains in the animal 3. Therefore, the waste products in the blood will pass through the blood capillaries on the peritoneum and enter the dialysate f1. The waste liquid f2 will be formed after a period of time.

Next, the first valve 111, the second valve 112 and the third valve 113 are opened. Then the waste liquid f2 may flow from the animal 3 to the Y-type duct joint 10, the first duct 15a, the first pressure sensor 17a, the first valve 111, the communication duct 14, the third valve 113, the output duct 13, the second air sensor 19b and the flow sensor 18 and finally be injected into the waste liquid container 4 by gravity or by the function of the second motor 16b. At the same time, the waste liquid f2 can also flow from the animal 3 to the Y-type duct joint 10, the second duct 15b, the second pressure sensor 17b, the second valve 112, the output duct 13, the second air sensor 19b and flow sensor 18 and finally be injected into the waste liquid container 4.

The operation method of the this example is a continuous cycle peritoneal dialysis. The operating modes of the first pressure sensor 17a, the second pressure sensor 17b, the flow sensor 18, the first air sensor 19a and the second air sensor 19b are similar those of EXAMPLE 1 and, therefore, not here repeated.

Example 4

Initially, the first valve 111 is closed and the second valve 112 and the third valve 113 are opened when performing the method. Next, the first motor 16a is started such that the dialysate f1 flows from the dialysate container 2 to the input duct 12, the first air sensor 19a, the communication duct 14, the third valve 113, the second valve 112, the second duct 15b, the second pressure sensor 17b and the Y-type duct joint 10. Finally, the dialysate f1 is injected into the live animal 3.

The dialysate f1 may remain in the animal 3 for a period of time. The diffusion exchange and the osmosis exchange take place in the animal 3 via the peritoneum of the animal 3 while the dialysate f1 remains in the animal 3. Therefore, the waste products in the blood will pass through the blood capillaries on the peritoneum and enter the dialysate f1. The waste liquid f2 will be formed after a period of time.

Next, the first valve 111, the second valve 112 and the third valve 113 are opened. Then the waste liquid f2 may flow from the animal 3 to the Y-type duct joint 10, the first duct 15a, the first pressure sensor 17a, the first valve 111, the communication duct 14, the third valve 113, the output duct 13, the second air sensor 19b and the flow sensor 18 and finally be injected into the waste liquid container 4 by gravity or by the function of the second motor 16b. At the same time, the waste liquid f2 can also flow from the animal 3 to the Y-type duct joint 10, the second duct 15b, the second pressure sensor 17b, the second valve 112, the output duct 13, the second air sensor 19b and flow sensor 18 and finally be injected into the waste liquid container 4.

The method of this example is a continuous cycle peritoneal dialysis. The operating modes of the first pressure sensor 17a, the second pressure sensor 17b, the flow sensor 18, the first air sensor 19a and the second air sensor 19b are similar to those of EXAMPLE 1 and, therefore, not here repeated.

Figure 2:
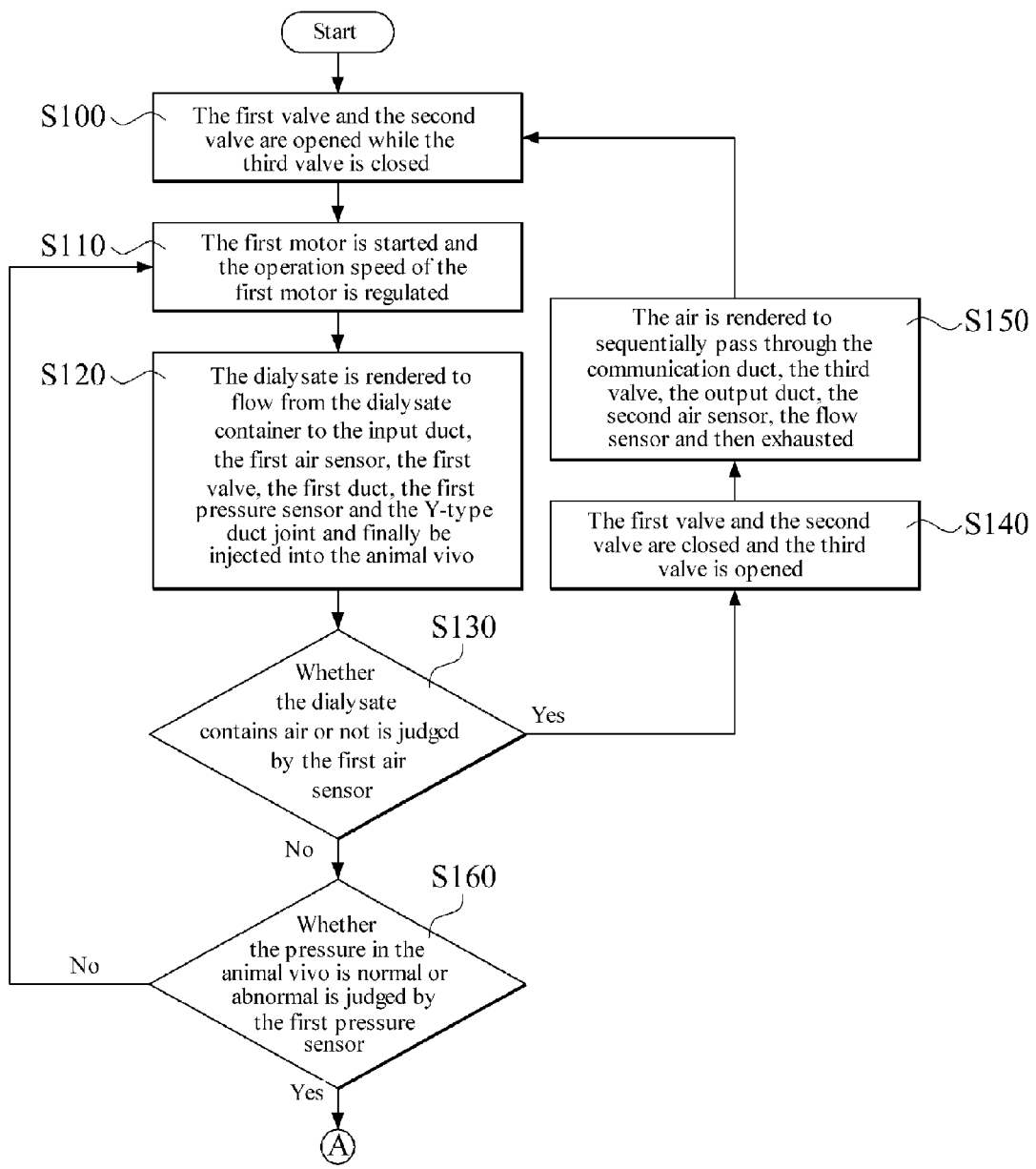
FIGS. 2 and 2A schematically illustrate flow charts of a method in accordance with an embodiment of the present disclosure.
Figure 2A:
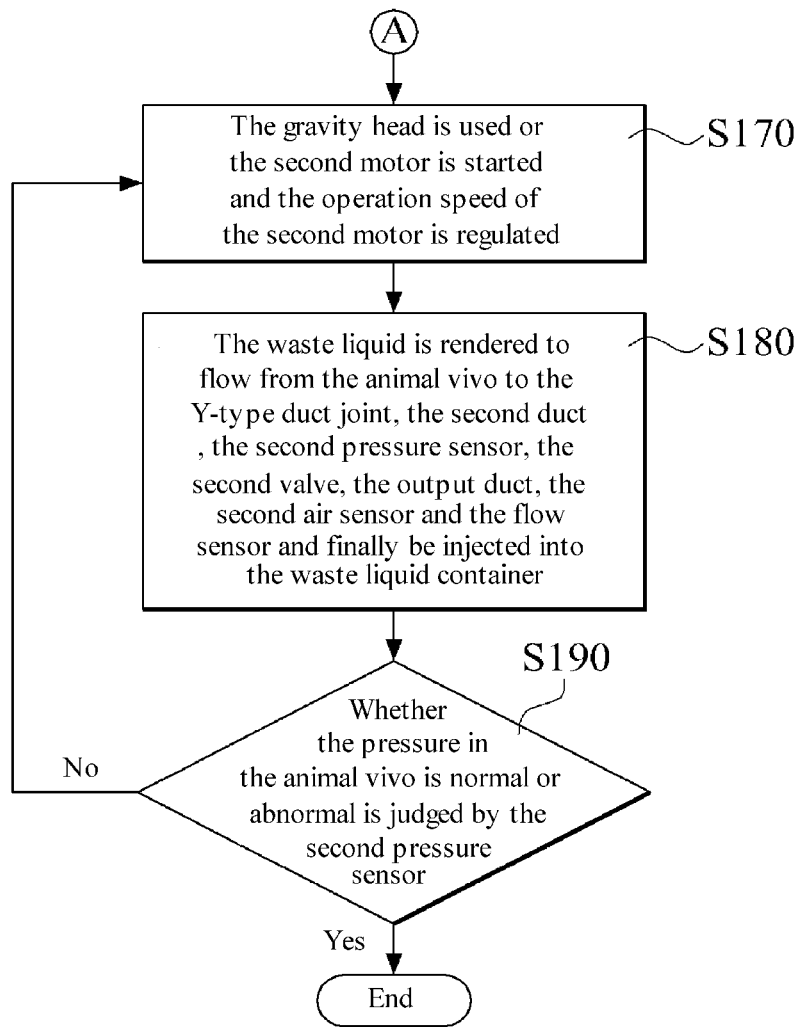

FIGS. 2 and 2A are flow charts for the techniques disclosed in EXAMPLE 1. The indicated reference characters appear in FIG. 1.

The first valve 111 and the second valve 112 are opened while the third valve 113 is closed (step S100).

The first motor 16a is started and the operation speed of the first motor 16a is adjusted (step S110).

The dialysate f1 is caused to flow from the dialysate container 2 to the input duct 12, the first air sensor 19a, the first valve 111, the first duct 15a, the first pressure sensor 17a and the Y-type duct joint 10 and finally be injected into the live animal 3 (step S120).

Whether the dialysate f1 contains air or not is determined by the first air sensor 19a (step S130).

The first valve 111 and the second valve 112 are closed and the third valve 113 is opened when the dialysate f1 contains air (step S140).

The air is caused to sequentially pass through the communication duct 14, the third valve 113, the output duct 13, the second air sensor 19b and the flow sensor 18 and then exhausted (step S150). Next, step S100 is performed again.

Whether the pressure in the animal 3 is normal or abnormal is determined by the first pressure sensor 17a when the dialysate f1 does not contain air (step S160).

The operation speed of the first motor 16a is regulated and step S110 is performed again when the pressure in the animal 3 is abnormal.

The gravity head is used or the second motor 16b is started and the operation speed of the second motor 16b is regulated when the pressure in the animal 3 is normal (step S170).

The waste liquid f2 is caused to flow from the animal 3 to the Y-type duct joint 10, the second duct 15b, the second pressure sensor 17b, the second valve 112, the output duct 13, the second air sensor 19b and the flow sensor 18 and finally be injected into the waste liquid container 4 (step S180).

Whether the pressure in the animal 3 is normal or abnormal is determined by the second pressure sensor 17b (step S190).

The operation speed of the second air sensor 19b is regulated and step S170 is performed again when the pressure in the animal 3 is abnormal.

Figure 3:
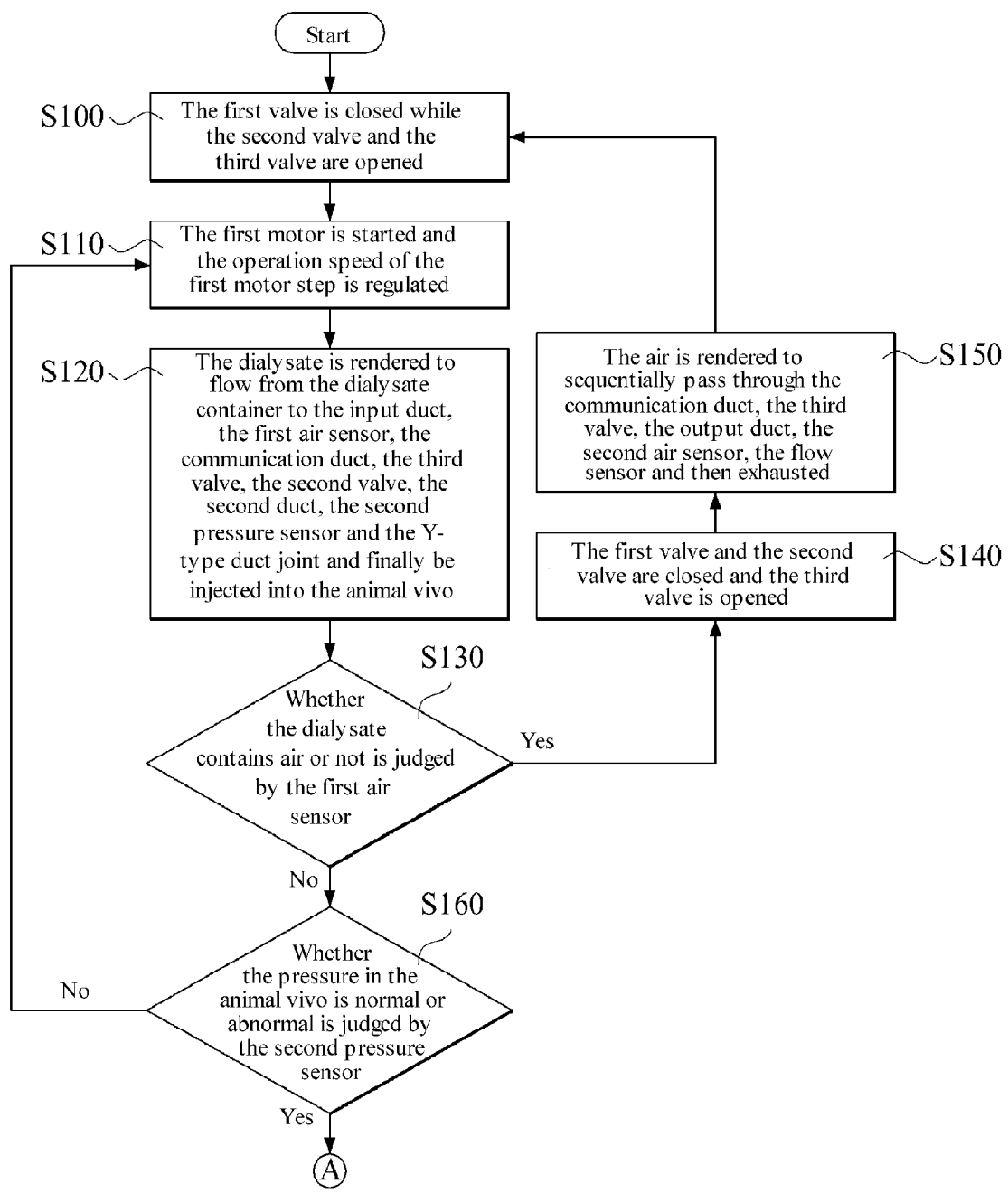
FIGS. 3 and 3A illustrate flow charts of a another method in accordance with an embodiment of the present disclosure.
Figure 3A:
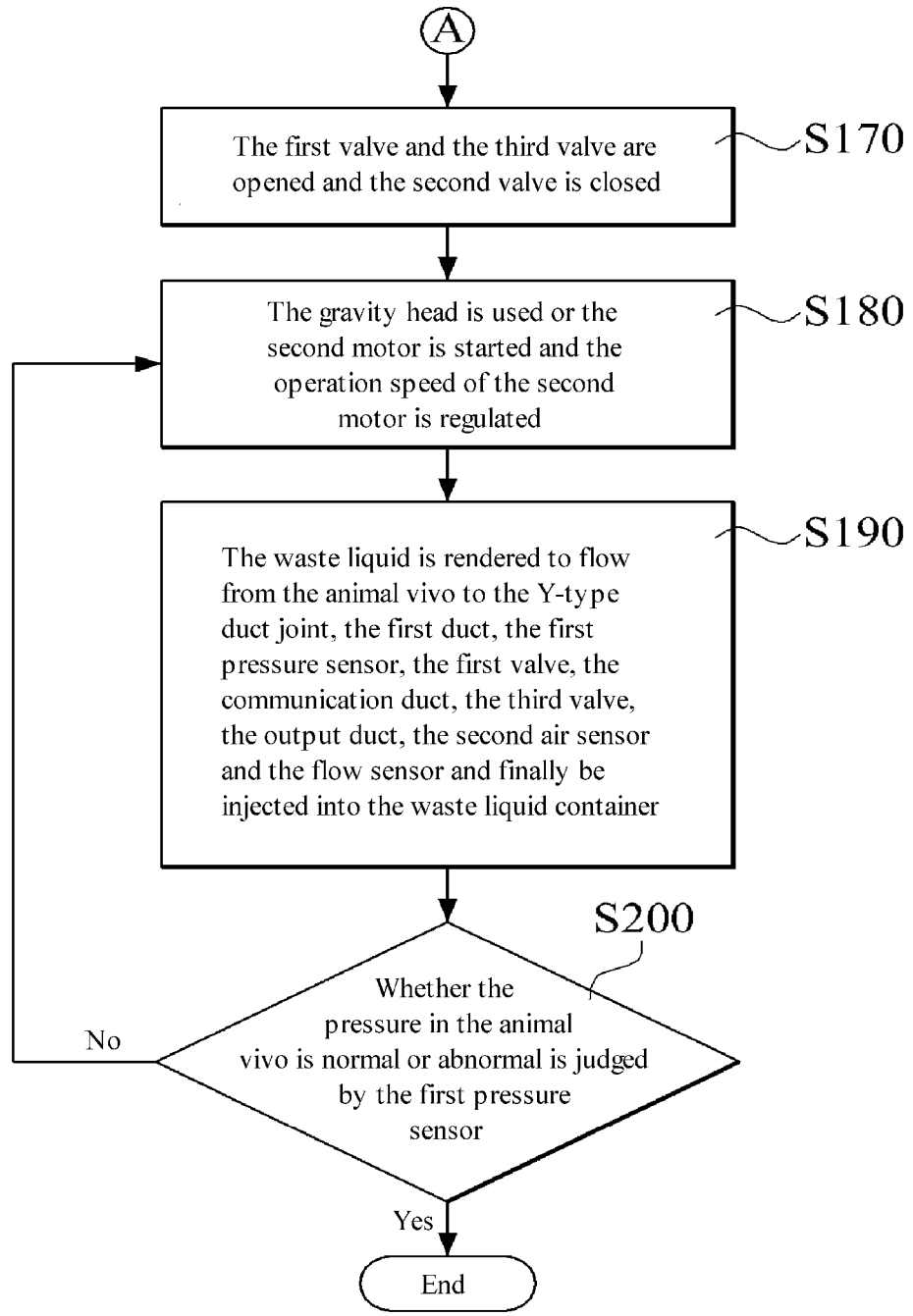

FIGS. 3 and 3A are flow charts for techniques disclosed EXAMPLE 2. The indicated reference characters appear in FIG. 1.

The first valve 111 is closed while the second valve 112 and the third valve 113 are opened (step S100).

The first motor 16a is started and the operation speed of the first motor 16a is adjusted (step S110).

The dialysate f1 is caused to flow from the dialysate container 2 to the input duct 12, the first air sensor 19a, the communication duct 14, the third valve 113, the second valve 112, the second duct 15b, the second pressure sensor 17b and the Y-type duct joint 10 and finally be injected into the live animal 3 (step S120).

Whether the dialysate f1 contains air or not is determined by the first air sensor 19a (step S130).

The first valve 111 and the second valve 112 are closed and the third valve 113 is opened when the dialysate f1 contains air (step S140).

The air is caused to sequentially pass through the communication duct 14, the third valve 113, the output duct 13, the second air sensor 19b and the flow sensor 18 and then exhausted (step S150). Next, step S100 is performed again.

Whether the pressure in the animal 3 is normal or abnormal is determined by the second pressure sensor 17b when the dialysate f1 does not contain air (step S160).

The operation speed of the first motor 16a is regulated and step S110 is performed again when the pressure in the animal 3 is abnormal.

The first valve 111 and the third valve 113 are opened and the second valve 112 is closed when the pressure in the animal 3 is normal (step S170).

The gravity head is used or the second motor 16b is started and the operation speed of the second motor 16b is adjusted (step S180).

The waste liquid f2 is caused to flow from the animal 3 to the Y-type duct joint 10, the first duct 15a, the first pressure sensor 17a, the first valve 111, the communication duct 14, the third valve 113, the output duct 13, the second air sensor 19b and the flow sensor 18 and finally be injected into the waste liquid container 4 (step S190).

Whether the pressure in the animal 3 is normal or abnormal is determined by the first pressure sensor 17a (step S200).

The operation speed of the second air sensor 19b is adjusted and step S180 is performed again when the pressure in the animal 3 is abnormal.

Figure 4:
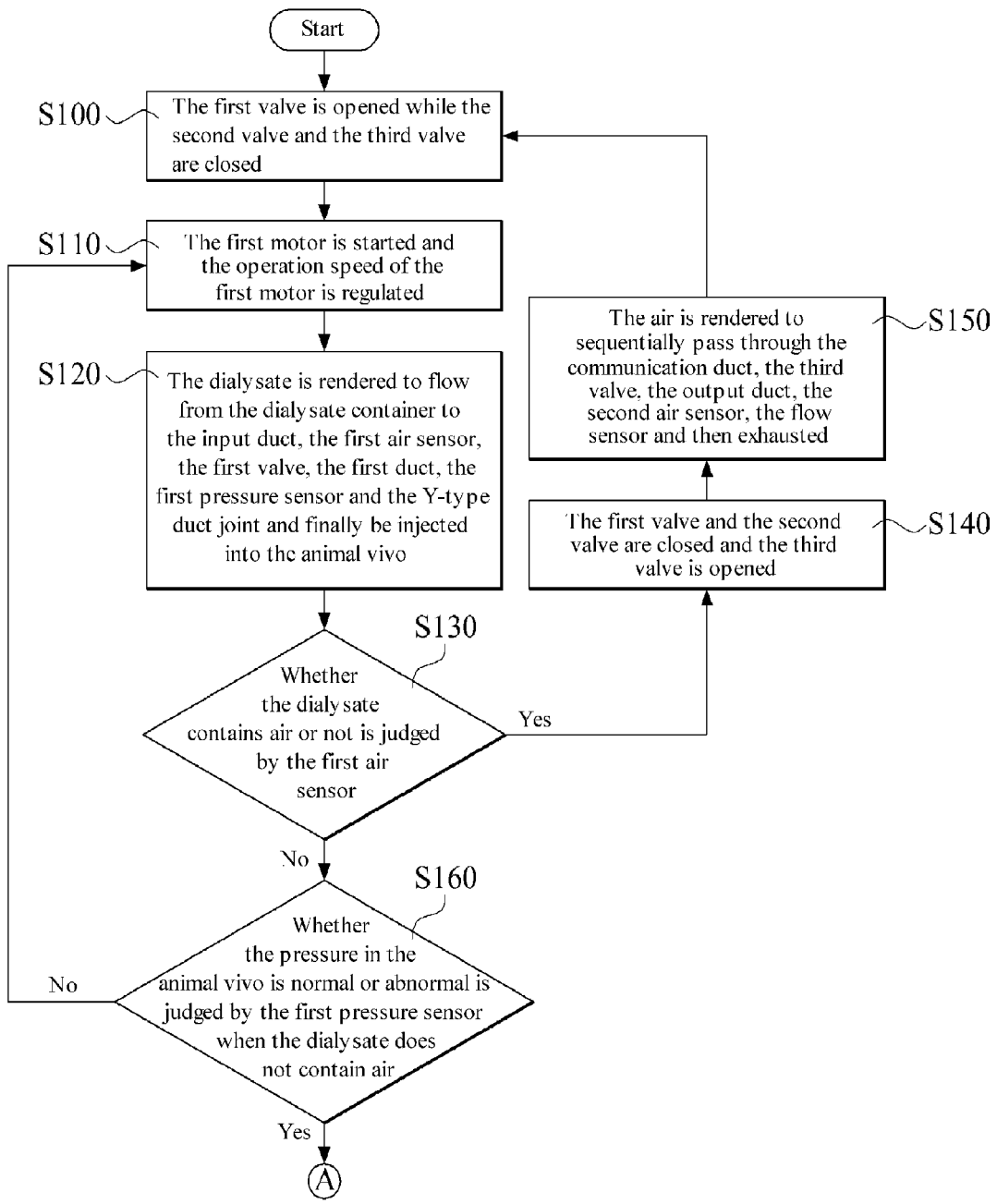
FIGS. 4 and 4A illustrate flow charts of a further method in accordance with an embodiment of the present disclosure.
Figure 4A:
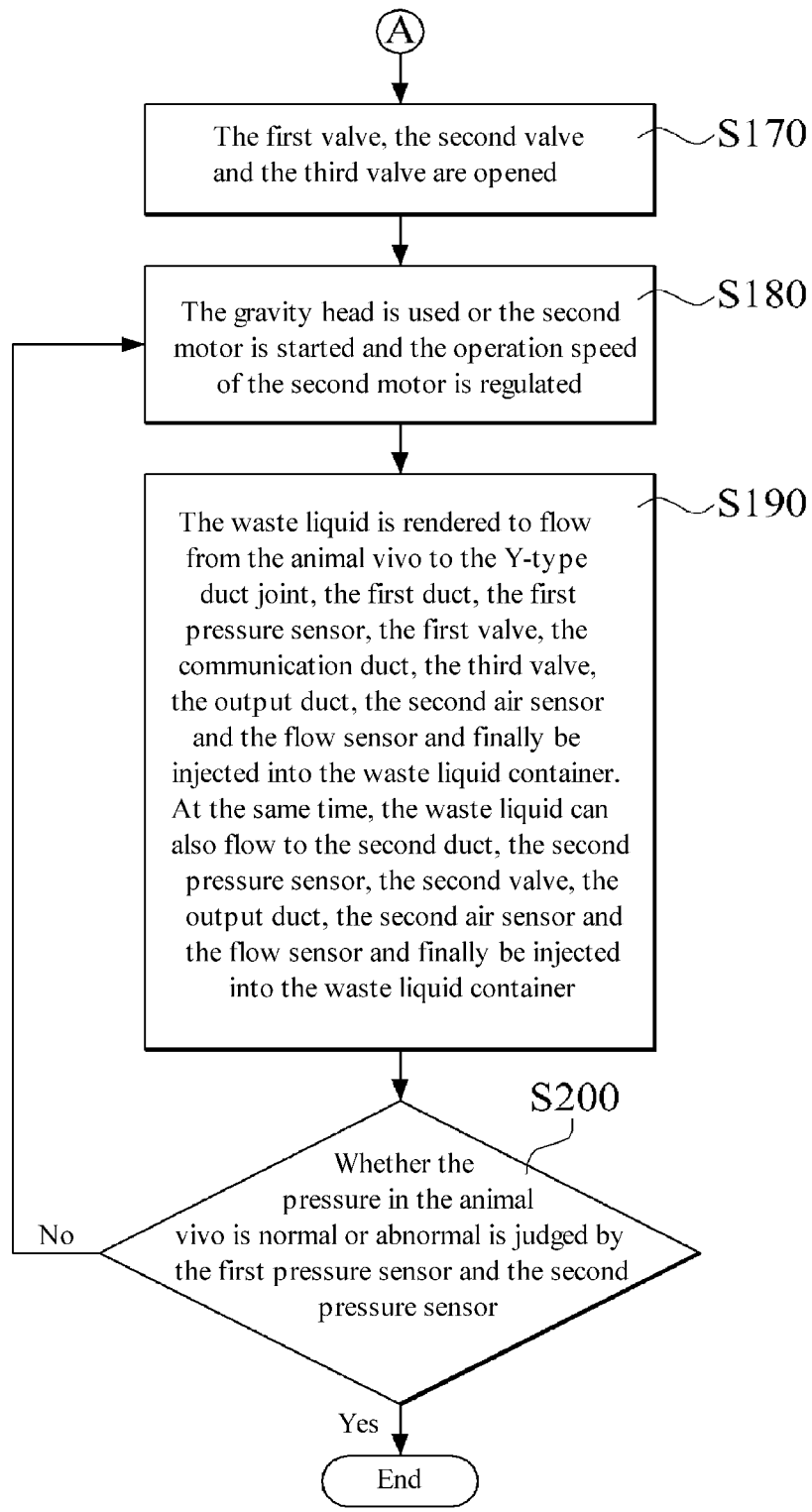

FIGS. 4 and 4A are flowcharts for techniques disclosed in EXAMPLE 3. The indicated reference characters appear in FIG. 1.

The first valve 111 is opened while the second valve 112 and the third valve 113 are closed (step S100).

The first motor 16a is started and the operation speed of the first motor 16a is adjusted (step S110).

The dialysate f1 is caused to flow from the dialysate container 2 to the input duct 12, the first air sensor 19a, the first valve 111, the first duct 15a, the first pressure sensor 17a and the Y-type duct joint 10 and finally be injected into the live animal 3 (step S120).

Whether the dialysate f1 contains air or not is determined by the first air sensor 19a (step S130).

The first valve 111 and the second valve 112 are closed and the third valve 113 is opened when the dialysate f1 contains air (step S140).

The air is caused to sequentially pass through the communication duct 14, the third valve 113, the output duct 13, the second air sensor 19b and the flow sensor 18 and then exhausted (step S150). Next, step S100 is performed again.

Whether the pressure in the animal 3 is normal or abnormal is determined by the first pressure sensor 17a when the dialysate f1 does not contain air (step S160).

The operation speed of the first motor 16a is regulated and step S110 is performed again when the pressure in the animal 3 is abnormal.

The first valve 111, the second valve 112 and the third valve 113 are opened when the pressure in the animal 3 is normal (step S170).

The gravity head is used or the second motor 16b is started and the operation speed of the second motor 16b is adjusted (step S180).

The waste liquid f2 is caused to flow from the animal 3 to the Y-type duct joint 10, the first duct 15a, the first pressure sensor 17a, the first valve 111, the communication duct 14, the third valve 113, the output duct 13, the second air sensor 19b and the flow sensor 18 and finally be injected into the waste liquid container 4. At the same time, the waste liquid f2 can also flow from the animal 3 to the Y-type duct joint 10, the second duct 15b, the second pressure sensor 17b, the second valve 112, the output duct 13, the second air sensor 19b and the flow sensor 18 and finally be injected into the waste liquid container 4 (step S190).

Whether the pressure in the animal 3 is normal or abnormal is determined by the first pressure sensor 17a and the second pressure sensor 17b (step S200).

The operation speed of the second air sensor 19b is adjusted and step S180 is performed again when the pressure in the animal 3 is abnormal.

Figure 5:
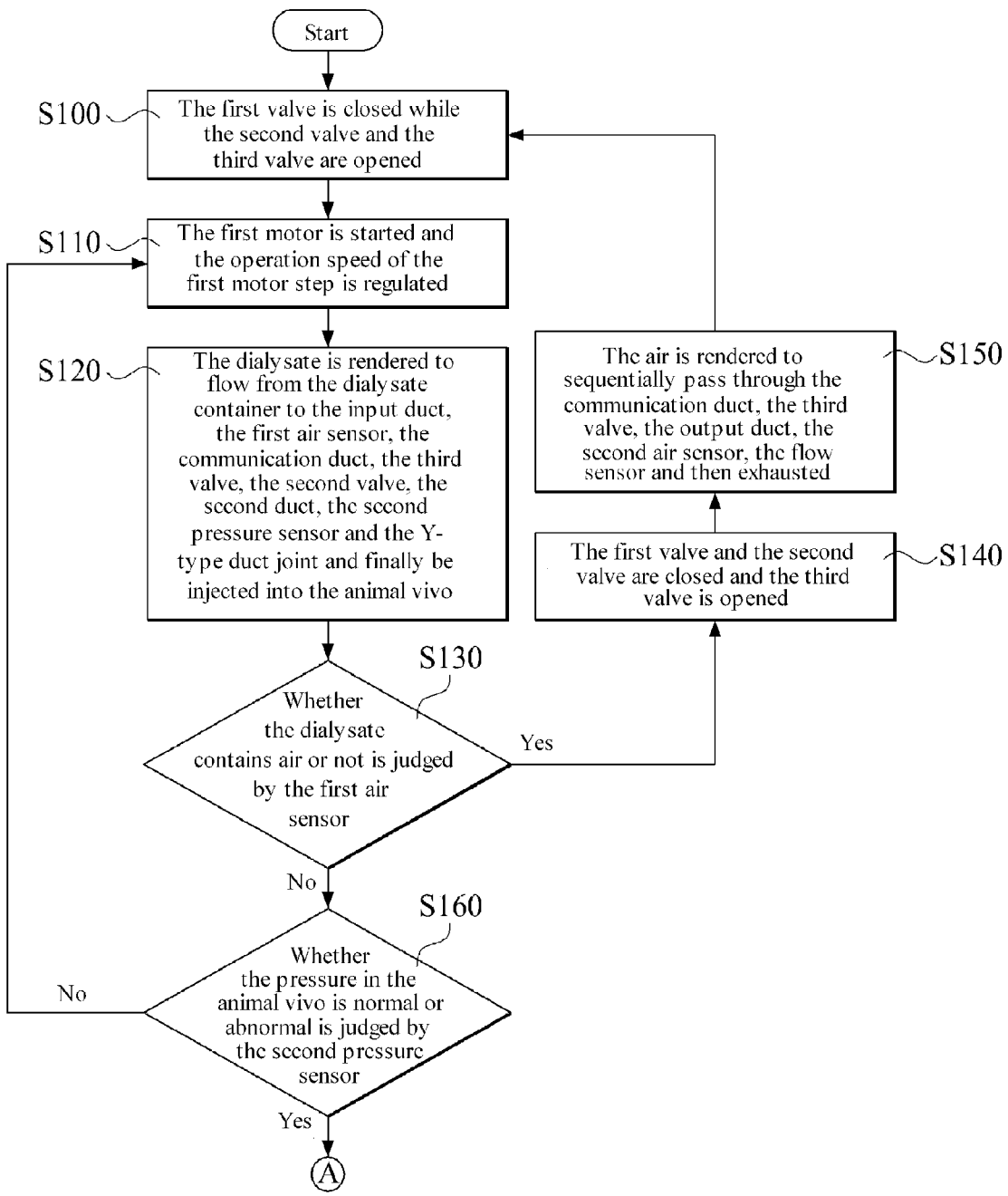
FIGS. 5 and 5A illustrate flow charts of another method in accordance with an embodiment of the present disclosure.
Figure 5A:
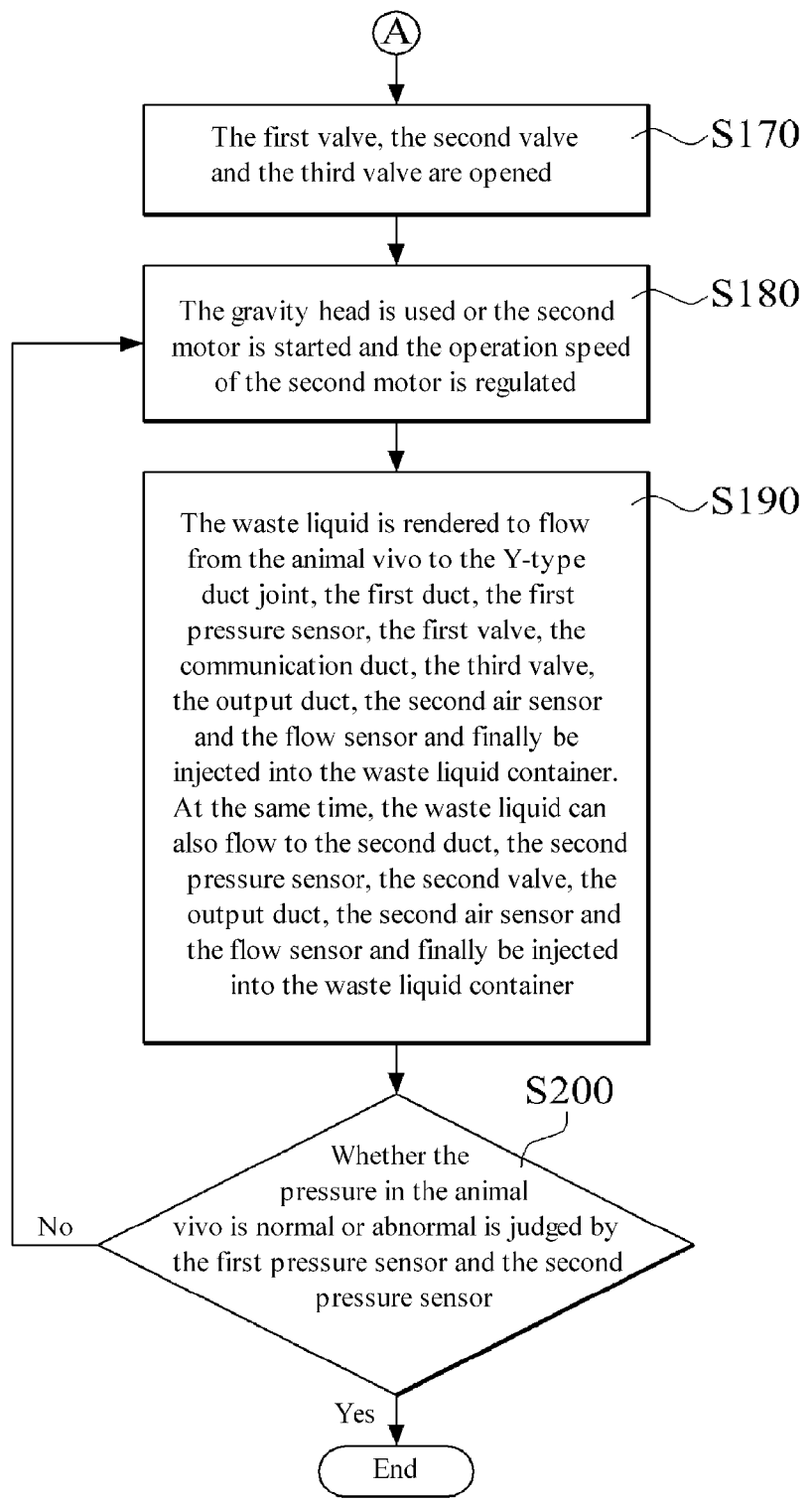

FIGS. 5 and 5A are flow charts for techniques disclosed in EXAMPLE 4. The indicated reference characters appear in FIG. 1.

The first valve 111 is closed while the second valve 112 and the third valve 113 are opened (step S100).

The first motor 16a is started and the operation speed of the first motor 16a is adjusted (step S110).

The dialysate f1 is caused to flow from the dialysate container 2 to the input duct 12, the first air sensor 19a, the communication duct 14, the third valve 113, the second valve 112, the second duct 15b, the second pressure sensor 17b and the Y-type duct joint 10 and finally be injected into the live animal 3 (step S120).

Whether the dialysate f1 contains air or not is determined by the first air sensor 19a (step S130).

The first valve 111 and the second valve 112 are closed and the third valve 113 is opened when the dialysate f1 contains air (step S140).

The air is caused to sequentially pass through the communication duct 14, the third valve 113, the output duct 13, the second air sensor 19b and the flow sensor 18 and then exhausted (step S150). Next, step S100 is performed again.

Whether the pressure in the animal 3 is normal or abnormal is determined by the second pressure sensor 17b when the dialysate f1 does not contain air (step S160).

The operation speed of the first motor 16a is regulated and step S110 is performed again when the pressure in the animal 3 is abnormal.

The first valve 111, the second valve 112 and the third valve 113 are opened when the pressure in the animal 3 is normal (step S170).

The gravity head is used or the second motor 16b is started and the operation speed of the second motor 16b is adjusted (step S180).

The waste liquid f2 is caused to flow from the animal 3 to the Y-type duct joint 10, the first duct 15a, the first pressure sensor 17a, the first valve 111, the communication duct 14, the third valve 113, the output duct 13, the second air sensor 19b and the flow sensor 18 and finally be injected into the waste liquid container 4. At the same time, the waste liquid f2 can also flow from the animal 3 to the Y-type duct joint 10, the second duct 15b, the second pressure sensor 17b, the second valve 112, the output duct 13, the second air sensor 19b and the flow sensor 18 and finally be injected into the waste liquid container 4 (step S190).

Whether the pressure in the animal 3 is normal or abnormal is determined by the first pressure sensor 17a and the second pressure sensor 17b (step S200).

The operation speed of the second air sensor 19b is regulated and step S180 is performed again when the pressure in the animal 3 is abnormal.

Since intelligent automatic peritoneal dialysis devices in accordance with embodiments of the present disclosure comprises first and second ducts, the dialysate and the waste liquid pass through different ducts, respectively, thereby improving dialysis efficiency. Additionally, since embodiments of the present disclosure comprise the flow direction control valve and a plurality of monitoring devices, the flow direction of the dialysate and the waste liquid are automatically controlled should a fault occur, thereby effectively solving the previously described problems.

The embodiments of the present disclosure can achieve several technical effects in the field of veterinary medicine, such as improved dialysis efficiency and automatic control of the dialysate flow directions of the dialysate and the waste liquid should a fault occur. However, the above disclosed embodiments are merely illustrative of the present invention. One skilled in the art may accomplish numerous modifications and verifications according to the present disclosure and within the spirit of the present invention.

In the preceding description, the present disclosure is described with reference to specifically exemplary embodiments thereof. It will, however, be evident that various modifications and changes may be made thereto without departing from the broader spirit and scope of the present disclosure, as set forth in the claims. The specification and drawings are, accordingly, to be regarded as illustrative and not as restrictive. It is understood that the present disclosure is capable of using various other combinations and embodiments and is capable of any changes or modifications within the scope of the inventive concept as expressed herein.

What is claimed is:

1. An intelligent automatic peritoneal dialysis device for delivering adialysate accommodated in a dialysate container into a live animal and removing a waste liquid from the animal into a waste liquid container, the intelligent automatic peritoneal dialysis device comprising:
    a flow direction control valve for controlling a flow direction of the dialysate and the waste liquid, the flow direction control valve having a first valve, a second valve and a third valve;
    an input duct connected to a dialysate container and the first valve, wherein the input duct causes dialysate flow from the dialysate container into the flow direction control valve;
    an output duct connected to a waste liquid container and the second valve, wherein the output duct causes waste liquid flow from the flow direction control valve into the waste liquid container;
    a communication duct having a first end directly connected to the input duct and a second end directly connected to the output duct, wherein the third valve is disposed in the communication duct, the first valve is in fluid communication with the dialysate container without passing through any of the second valve and the third valve, the second valve is in fluid communication with the waste liquid container without passing through any of the first valve and the third valve, and the third valve is in fluid communication with the dialysate container and the waste liquid container without passing through any of the first valve and the second valve;
    a first motor disposed between the dialysate container and the input duct such that the dialysate may flow from the dialysate container to the input duct by operation of the first motor; and
    a second motor disposed between the waste liquid container and the output duct such that the waste liquid may flow from the output duct to the waste liquid container by operation of the second motor;
    a first duct directly connected to the first valve and capable of being connected to the animal; and
    a second duct connected to the second valve and capable of being connected to the animal.

2. The device of claim 1, further comprising:
    a first pressure sensor disposed in the first duct, for monitoring a pressure of the animal to regulate an operation speed of the first motor; and
    a second pressure sensor disposed in the second duct, the second pressure for monitoring the pressure of the animal to regulate an operation speed of the second motor.

3. The device of claim 1, further comprising a flow sensor disposed in the output duct, wherein the flow sensor monitors a flow of the waste liquid so as to regulate an operation speed of the second motor.

4. The device of claim 1, further comprising:
    a first air sensor disposed in the input duct, wherein the first air sensor monitors whether the dialysate flowing through the input duct contains air or not; and
    a second air sensor disposed in the output duct, wherein the second air sensor monitors whether the waste liquid flowing through the output duct contains air or not.

5. The device of claim 1, further comprising a Y-type duct joint having one end connected to the first duct and the second duct and the other end for extending into the animal.

6. A method of operating the device of claim 1, the method comprising:
    (a) opening the first valve and the second valve while closing the third valve;
    (b) causing the dialysate from the dialysate container to flow through the input duct, the first valve and the first duct and be injected into the animal; and
    (c) causing the waste liquid from the animal to flow through the second duct, the second valve and the output duct and be injected into the waste liquid container.

7. A method of operating the device of claim 1, the method comprising:
    (a) closing the first valve while opening the second valve and the third valve;

(b) causing the dialysate from the dialysate container to flow through the input duct, the communication duct, the third valve, the second valve and the second duct and be injected into the animal;

(c) opening the first valve and the third valve while closing the second valve; and (d) causing the waste liquid from the animal to flow through the first duct, the first valve, the communication duct, the third valve and the output duct and be injected into the waste liquid container.

8. A method of operating the device of claim 1, the method comprising:

(a) opening the first valve while closing the second valve and the third valve;

(b) causing the dialysate from the dialysate container to flow through the input duct, the first valve and the first duct and be injected into the animal;

(c) opening the first valve, the second valve and the third valve; and (d) causing the waste liquid from the animal to flow through the first duct, the first valve, the communication duct, the third valve and the output duct and be injected into the waste liquid container while at the same time, the waste liquid from the animal can also flow through the second duct, the second valve and the output duct and be injected into the waste liquid container.

9. A method of operating the device of claim 1, the method comprising:

(a) closing the first valve while opening the second valve and the third valve;

(b) causing the dialysate from the dialysate container to flow through the input duct, the third valve, the second valve and the second duct and be injected into the animal;

(c) opening the first valve, the second valve and the third valve; and (d) causing the waste liquid from the animal to flow through the first duct, the first valve, the communication duct, the third valve and the output duct and be injected into the waste liquid container while at the same time, the waste liquid from the animal can also flow through the second duct, the second valve and the output duct and be injected into the waste liquid container.

10. A method of operating the device of claim 1, the method comprising:

(a) controlling the flow direction control valve such that at least one of the first valve, the second valve and the third valve is an opening valve;

(b) causing the dialysate from the dialysate container to flow through the input duct, the flow direction control valve, and at least one of the first duct and the second duct and be injected into the animal; and (c) causing the waste liquid from the animal to flow through at least one of the first duct and the second duct, the flow direction control valve, and the output duct and be injected into the waste liquid container.

* * * * *